United States Patent [19] [11] 3,988,204
Andreasen et al. [45] Oct. 26, 1976

[54] PRODUCTION OF GLUCOAMYLASE FOR CONVERSION OF GRAIN MASHES IN THE PRODUCTION OF GRAIN SPIRITS

[75] Inventors: Arthur A. Andreasen; Albert J. Bronsky; Wendell L. Bruce, all of Louisville, Ky.

[73] Assignee: Joseph E. Seagram & Sons, Inc., New York, N.Y.

[22] Filed: Oct. 31, 1974

[21] Appl. No.: 519,560

[52] U.S. Cl. ............................ 195/15; 195/16; 195/31 R; 195/37; 195/66 R; 426/11; 426/13; 426/29
[51] Int. Cl.² ................ C12C 11/00; C07G 7/028
[58] Field of Search ............... 195/21, 31 R, 16, 13, 195/66 R, 37, 15; 426/28, 29, 11, 14, 13

[56] References Cited
UNITED STATES PATENTS

| | | | |
|---|---|---|---|
| 3,301,768 | 1/1967 | Smiley | 195/66 R |
| 3,337,414 | 8/1967 | Wilson | 195/31 R |
| 3,418,211 | 12/1968 | Van Lanen et al. | 195/31 R |
| 3,783,100 | 1/1974 | Larson et al. | 195/31 R |
| 3,806,415 | 4/1974 | Hayes | 195/31 R |
| 3,868,307 | 2/1975 | Van Lanen et al. | 195/31 R X |

*Primary Examiner*—David M. Naff
*Attorney, Agent, or Firm*—Kane, Dalsimer, Kane, Sullivan and Kurucz

[57] ABSTRACT

Grain alcohol is produced from a mash of high cereal grain content by cooking a dispersion of cereal grains in water at a temperature of about 300° to 350° F under a pressure of about 50–120 psig, converting the cooked mash with a glucoamylase ferment produced by *A. awamori* NRRL 3112 and fermenting the converted mash with yeast to produce grain alcohol. The glucoamylase ferment is preferably produced by propagation of *A. awamori* NRRL 3112 on a mash of cereal grains dispersed in water which has been cooked at the same pressure and temperature used for cooking of the mash when producing grain alcohol.

17 Claims, No Drawings

PRODUCTION OF GLUCOAMYLASE FOR CONVERSION OF GRAIN MASHES IN THE PRODUCTION OF GRAIN SPIRITS

BACKGROUND OF THE INVENTION

1. Field of the Invention

The invention concerns the production of grain spirits from grain mashes and more particularly concerns a process for obtaining high yields of the starch hydrolysing enzyme glucoamylase by incubation of *A. awamori* NRRL 3112 in grain mash and using the yield to convert grain mash.

2. Brief Description of the Prior Art

Commercial processes for the production of alcohol from mashes of high cereal grain content without employing an amylo enzyme producing microorganism are well known; see for example, U.S. Pat. No. 2,375,189.

Processes for converting high grain content mashes with the assistance of a microorganism product are also known; see for example, U.S. Pat. Nos. 3,303,102 and 3,418,211. U.S. Pat. No. 3,301,768 discloses the use of the microorganism *A. awamori* NRRL 3112 to obtain propagation ferments which are useful in converting high cereal grain content mashes. The ferment propagation mediums and mash to be converted are cooked under relatively low temperatures and pressures.

SUMMARY OF THE INVENTION

The invention comprises in a process for preparing grain alcohol by (a) cooking a dispersion of cereal grains in water to obtain a mash of high cereal grain content, (b) converting the mash thereby obtained with a glucoamylase ferment produced by the action of the microorganism *A. awamori* NRRL 3112 on a mash obtained by cooking a dispersion of cereal grains and (c) fermenting the converted mash, the improvement which comprises; in step (a), cooking the grain dispersion under a pressure substantially in excess of atmospheric pressure.

By the improved process of the invention, glucoamylase ferments obtained from the cultivation of *A. awamori* NRRL 3112 show about a 100 percent increase in enzyme activity. In addition, by the improved process of the invention the number of glucoamylase units required for conversion of high grain content mashes is reduced by about 50 percent. A unit of glucoamylase activity is that quantity of glucoamylase necessary to form 1 gram of glucose from a 4 percent starch solution, in 1 hour, at 60° C. The smaller amount of glucoamylase ferment required for converting mashes provides an economic and operating advantage in the process of preparing grain alcohol.

Employment of glucoamylase ferments prepared according to the invention are also advantageous in that when added to the mash for yeast propagation prior to inoculation with yeast, the yeast mash will have a significantly higher yeast cell count. In addition, as a result of the improved yeast growth, when the admixture of glucoamylase ferment and yeast is inoculated into a mash to be fermented, the volume of yeast inoculum required may be proportionately reduced. This, of course, is an economic and operating advantage not associated with the methods of the prior art.

DETAILED DESCRIPTION OF THE INVENTION

The improved process of the invention is carried out by adding to a pressure cooked high grain content mash, a propagated ferment of high glucoamylase activity and inoculating with sufficient yeast culture to saccharify and ferment the mash under conventional incubation conditions. The term "high grain content mash" as used herein, means a mash containing circa 24 grams of cereal grain for each 100 milliliters of mash. By "conventional incubation conditions" we mean that the fermentation is carried out employing conventional fermentation equipment and at a temperature and for a period of time sufficient to effect the fermentation.

The mash is prepared by slurrying an appropriate cereal grain such as corn in water. The slurry is then pressure cooked employing conventional batch pressure cooking apparatus or preferably continuous pressure cooking apparatus. In general, cooking is carried out at a relatively high temperature range of from about 300° to about 350° F. and under a pressure of from about 50 to about 120 psig. In general, the pressure under which continuous cooking of the mash is carried out will be determined by the temperature selected since it is advantageous to employ a pressure which is sufficiently above the vapor pressure of the cooking mixture so as to prevent flashing within the cooker, about 5 psig above that pressure at which flashing would occur.

The length of time required to obtain the pressure-cooked mash employed in the method of the invention under the temperature and pressure conditions described above will vary within certain limits, depending on overall operating parameters. In general, it has been found that the time of cooking is advantageously selected so as to be inversely proportional to the temperature employed in cooking the mash. More specifically, the pressure cooking of the mash is preferably carried out for a period of time ranging from about 30 minutes when the temperature employed is circa 300° F. to about 5 minutes when the temperature employed is circa 350° F. Specific optimal cooking times for cooking at temperatures intermediate between 300° and 350° F. may be readily determined by trial and error. Most advantageously, cooking is carried out for about 3.2 minutes at a temperature of about 320° F. and under a pressure of about 80 psig, however those skilled in the art will appreciate that there may be some variance in specific times required for optimal cooking at a given temperature or pressure, depending upon the size of the cooker, meal particle size, throughput rates (in a continuous cooker) and like variables in any cooking operation.

Advantageously, the pH of the mash being cooked is adjusted within the range of from about 5.0 to about 5.6, and to circa 5.0 prior to addition of the propagation ferment and inoculation with yeast as hereinafter described. The pH of the mash may be adjusted by the addition of stillage or other acidic materials such as mineral or organic acids such as sulfuric acid or citric acid. The propagation ferment added for conversion of the pressure-cooked mash described above is prepared by incubating the microorganism *A. awamori* NRRL 3112 on a substrate of high grain content mash, prepared by cooking a grain dispersion under relatively high temperature and pressure conditions. The pressure cooked mash employed as the propagator medium may be the same mash or mash prepared in the same manner as described above for preparing the mash to be converted. Incubation is carried out employing conventional aeration apparatus and at a temperature within the range of from about 90° to about 100° F. Advantageously, incubation is carried out upon a mash medium having a pH within the range of from about 4.0 to about 5.5, preferably about 4.8. Adjustments of the pH may be carried out by the addition of stillage or other acidic materials such as mineral or organic acids such as sulfuric or citric acids, respectively.

The amount of propagation ferment added to the mash in accordance with the improved method of the invention may be varied. In general, however, the amount required provides at least 400 units of glucoamylase per bushel of grain in the mash. The precise amount employed for an optimum alcohol yield will of course depend on the amount of liquefying malt employed in the process of the invention.

In a preferred embodiment of the process of the invention, glutamic acid or monosodium glutamate is added either to the glucoamylase propagator inoculum medium or to the starting *A. awamori* NRRL 3112 culture medium employed for the inoculation of the propagator inoculum. Generally, the glutamic acid or monosodium glutamate is added in a proportion of about 0.5 percent (w/v) of the propagation medium based on glutamic acid and results in enhanced yields of glucoamylase.

The following examples describe the manner and process of making and using the invention and set forth the best mode contemplated by the inventors of carrying out the invention but are not to be construed as limiting. All percentages shown are by weight unless otherwise stated.

EXAMPLE 1

Laboratory Glucoamylase Propagation In Plant Produced Pressure Cooked Mash

A — Starter Culture

Spores obtained from a stock culture of *A. awamori* NRRL 3112 (maintained on Czapek's agar) are transferred to a starter culture medium consisting of 5 percent corn and 0.5 percent yeast extract in water, adjusted initially to a pH of about 4.8. The inoculated starting material is shaken and maintained at about 72° F. Two subcultivations are made at 30 and 48 hours respectively.

Part B — Propagator Medium

A slurry of corn amounting to about 97% of the total grain is cooked in a ratio of 15 gallons of liquid per bushel of grain and subsequently liquified with 3% malt. Sufficient stillage is added to adjust the pH of the slurry to about 5.3. The mash is cooked for 3.2 minutes at a temperature of 320° F. while being subjected to a pressure of 80 psig. Cooking is carried out in a continuous plant pressure-cooker.

Part C — Propagation

A 30 liter aerobic propagating vessel is charged with 21 liters of the pressure-cooked mash obtained in Part B, supra., the pressure cooked mash is reduced from 21.6° to 20° balling with tap water, sterilized at 250° F. for 30 minutes and then cooled to a temperature of circa 95° F. The sterilized mash is then inoculated with 2.4 percent of the second stage (48 hour) shake culture of *A. awamori* NRRL 3112 (as prepared in Part A above). The inoculated pressure cooked mash is agitated by means of turbine-type impellors at 600 rpm, and aerated at 0.5 volume of air per volume of liquid per minute while the mash temperature is maintained at 95° F. Volume of the mixture is maintained constant by the periodic addition of sterile water. After 151 hours of incubation, there is obtained a glucoamylase rich ferment having a pH of 3.8 and a glucoamylase activity of 15.4 units per milliliter.

EXAMPLE 2

Laboratory Glucoamylase Propagation in Plant Pressure-Cooked Mesh

Part A — Starter Culture

A starter culture is prepared following the procedure given in Example 1, Part A.

Part B — Propagator Medium

A corn grain slurry containing sufficient stillage for pH adjustment to 5.3 and at a 16 gallon of liquid per bushel of corn ratio is pressure cooked in a continuous cooking system at 320° F. and under a pressure of 80 psig for 3.2 minutes. The mash is liquefied and partially converted with 2 percent malt at 145° F. The mash is then sterilized in a laboratory propagator at a temperature of circa 250° F. for 30 minutes and cooled to incubation temperatures (circa 95° F). A mash of 28 gallons per bushel of grain in the ratio of 98 percent corn and 2 percent malt is obtained.

Part C — Propagation

The sterilized, pressure cooked mash of Part B above is inoculated with 2.4 percent of the second stage (48 hour) shake culture of *A. awamori* NRRL 3112 prepared according to Part A above. The inoculated pressure cooked mash is agitated by means of turbine-type impellors at 600 rpm, and aerated at 0.5 volume of air per volume of liquid per minute while the mash temperature is maintained at 95° F. The volume of the mixture is maintained constant by the periodic addition of sterile water. After 180 hours, there is obtained a glucoamylase rich ferment having a pH of 3.3 and a glucoamylase activity of 18.5 units per milliliter.

EXAMPLE 3

Plant Run No. 1

Part A — Starter Culture

Following the procedure of Example 1, Part A there is obtained a starter culture medium of *A. awamori* NRRL 3112.

Part A-1 — Propagator Inoculum

Soured yeast mash of any conventional proportions of grain and water and as conventionally prepared for the growth of yeast inoculum is charged into a stainless steel, unbaffled, 90 gallon propagator equipped for air admission through a tube sparger and for agitation with one turbine-type impellor rotating at 90 rpm. The mash is diluted with water to 6° balling resulting in 70 to 90 gallons of mash which is sterilized at 250° F. for one-half hour and cooled to inoculation temperature. About 1% of the mash volume or 3 liters of second stage starter culture prepared according to Part A above is used to inoculate the propagator contents. The propagator is then held at 75° to 80° F. under 6 to 10 psig of positive pressure and aerated at 1 to 2 cubic feet per minute for a period of 30 to 40 hours.

Part B — Propagator Medium

A corn grain slurry containing sufficient stillage for pH adjustment to 5.0 at a 16 gallon of liquid per bushel of grain ratio is pressure cooked in a continuous cooking system at a temperature of 320° F. and under a pressure of 80 psig for 3.2 minutes. The mash is liquefied and partially converted with 3 percent malt at 145° F. There is thus obtained a mash of 28 gallons per bushel of grain in the ratio of 97 percent corn and 3 percent malt.

Part C — Propagation

To a stainless steel, baffled, 6000 gallon propagator equipped for air admission through a ring sparger and for agitation with two turbine-type impellors rotating at 90 rpm there is charged 4600 gallons of mash prepared according to Part B above. The propagator contents are sterilized for one-half hour at 248° F., cooled to 95° F. and then inoculated with circa 1.5 percent by volume of the propagator inoculum prepared according to Part A-1 above. The propagator is held at 94° to 96° F. under 6 to 10 pounds of positive pressure and aerated at about 300 cubic feet per minute (0.45 volumes of air per volume of liquid per minute) for a period of 180 hours. At periodic intervals during the incubation, samples of the ferment are taken and analyzed for pH and glucoamylase activity. The results are listed in Table 1a as follows:

Table 1a

| Incubation Time Hours | (Run No. 1) pH | Glucoamylase Activity units/ml |
|---|---|---|
| 0 | 5.0 | — |
| 85 | 3.8 | 6.1 |
| 108 | 3.6 | 8.3 |
| 132 | 3.6 | 10.8 |
| 156 | 3.5 | 14.6 |
| 180 | 3.5 | 16.0 |

Plant Run No. 2

Similarly, repeating the above procedure, a second run is obtained with the following results shown in Table 1b.

Table 1b

| Incubation Time Hours | (Run No. 2) pH | Glucoamylase Activity units/ml |
|---|---|---|
| 0 | 5.0 | — |
| 72 | 3.9 | 6.0 |
| 108 | 3.6 | 10.3 |
| 132 | 3.6 | 12.0 |
| 156 | 3.5 | 14.4 |
| 180 | 3.5 | 15.4 |
| 204 | 3.4 | 16.3 |

As shown in Tables 1a and 1b, after 180 hours, the glucoamylase activity is 16.0 units per milliliter for Plant Run 1 (Table 1a) and 15.4 units per milliliter for Plant Run 2 (Table 1b). These yields are nearly double the average obtained in runs carried out following the above procedure but using mash cooked at atmospheric pressures.

EXAMPLE 4

Fermentation of Plant Mashes Converted With Glucoamylase to Produce Grain Alcohol Plant Run No. 1

A series of fermenters are charged with mashes prepared by cooking slurries of corn for 3.2 minutes at a temperature of 320° F. and under a pressure of 80 psig. The pressure cooked mash is then liquefied with 2 to 3 percent gibberellin treated malt at 145° F. and cooled to fermentation temperatures. The mash so obtained contains 97 to 98 percent corn, a pH of about 5.0 and a mash ratio of 28 gallons per bushel of grain. The fermenters are then inoculated with a 1 percent (by volume) yeast culture (200 million yeast cells per ml.) and varying quantities of the glucoamylase rich ferment obtained in Example 3 supra.. The fermentation is carried out by maintaining the temperature at about 90° F. The amounts of malt and glucoamylase ferment employed and the alcohol yields obtained are listed in Table 2a below:

Table 2a

| | Plant Run No. 1 | | | |
|---|---|---|---|---|
| Malt % | Conversion Agent Glucoamylase units/bu | ml/bu | No. of Fermenters | Alcohol Proof gals/bu |
| 3 | 1536 | 97 | 4 | 5.24 |
| 3 | 1024 | 65 | 45 | 5.31 |
| 3 | 640 | 41 | 103 | 5.32 |
| 3 | 416 | 26 | 4 | 5.26 |
| 2 | 960 | 60 | 2 | 5.24 |

As shown in Table 2a, all levels of glucoamylase gave approximately the same alcohol yield. Therefore, 416 units per bushel or 26 milliliters per bushel of an enzyme ferment prepared in accordance with the improved process of the invention and having 16 units of glucoamylase activity per milliliter was sufficient for conversion of pressure cooked mash.

Plant Run No. 2

Similarly, repeating the above procedure but admixing the yeast mash with the glucoamylase enzyme ferment gave results as shown in Table 2b below:

Table 2b

| | Plant Run No. 2 | | | |
|---|---|---|---|---|
| Malt % | Conversion Agent Glucoamylase units/bu | ml/bu | No. of Fermenters | Alcohol Proof gals/bu |
| 3 | 1062 | 59 | 41 | 5.31 |
| 3 | 708 | 39 | 10 | 5.30 |
| 2 | 1062 | 59 | 14 | 5.25 |
| 1½ | 1062 | 59 | 39 | 5.24 |
| 1½ | 708 | 39 | 8 | 4.91 |

As shown in Table 2b, both levels of glucoamylase with 3% malt gave approximately the same alcohol yield when used at the same level as in Run 1 (Table 2a) above; 708 units per bushel or 39 milliliters per bushel were sufficient for maximum yield. At the 2 percent or 1½ percent malt level, 1062 units per bushel or 59 milliliters per bushel were sufficient for a normal alcohol yield, but 708 units or 39 milliliters per bushel at 1.5% malt apparently is insufficient.

However, following the above procedure but replacing in both the glucoamylase propagation medium and the fermentation medium, the pressure-cooked mash as used therein, with equal proportion of mash cooked at atmospheric pressures and the ferment having a glucoamylase activity of 8 units per milliliter, it is found that at 3% malt levels, 1200 units per bushel or 134 milliliters per bushel of enzyme culture is required to obtain similar results.

From the foregoing, it is apparent that the pressure cooked mash gives a higher yield of enzyme and that less enzyme is required for fermentation than when atmospherically cooked mash is used. It is also apparent that glucoamylase requirements increase when the malt percentage is decreased and less glucoamylase is required as the malt concentration of the mash is increased.

It was also noted that the yeast count in Run No. 2 (wherein the yeast mash was admixed with the glucoamylase enzyme prior to yeast growth) was increased by 50%, i.e. from 200,000,000 per milliliter to 300,000,000 per milliliter in comparison to the yeast count found in the yeast culture used to inoculate fermentations of Run No. 1. Therefore, one-third less volume of yeast inoculum could be used.

EXAMPLE 5

Laboratory Fortification With Glutamic Acid

Part A — Starter Culture

A starter culture of *A. awamori* NRRL 3112 is prepared following the procedure set forth in Example 1, Part A.

Part B — Propagation Medium

A propagation medium is prepared following the procedure set forth in Example 2, Part B with the exception that 0.7% monosodium glutamate, equivalent to 0.5 percent by weight of glutamic acid is added to the mash before sterilization.

Part C — Propagation

Following the procedure set forth in Example 2, Part C, the propagation medium of Part B above is inoculated with 2.4 percent of the shake culture (48 hour) prepared in Part A above and incubated according to the procedure set forth in Example 2, Part C. After 180 hours of incubation there is obtained a glucoamylase ferment having about a 10 percent increase in glucoamylase activity per milliliter in comparison to a control propagation lacking the added glutamic acid in the propagation medium, i.e.; 20.8 vs. 18.5 units/ml.

What is claimed is:

1. A process for preparing grain alcohol, which comprises;
    a. cooking a dispersion of cereal grains in water under a pressure of between about 50 to 120 psig and at a temperature within the range of from about 300° to about 350° F. to obtain a mash of high cereal grain content, said grain consisting essentially of 97 to 99 percent corn;
    b. converting the mash obtained in step (a) above with a glucoamylase ferment produced by the propagation of the microorganism *A. awamori* NRRL 3112 on a mash obtained by cooking a grain dispersion consisting essentially of 97 to 99 percent corn, under a pressure of from 50 to 120 psig and at a temperature of from about 300° to about 350° F., said ferment being the product produced by the propagation fermentation of said organism on said mash to which there is added prior to propagation about 0.5 percent (w/v) of a compound selected from the group consisting of glutamic acid and monosodium glutamate;
    c. inoculating the converted mash with fermentation yeast; and
    d. fermenting the inoculated and converted mash for a sufficient period to produce grain alcohol.

2. A process according to claim 1 wherein the grain dispersion in step (a) is cooked under a pressure of about 80 psig.

3. A process for preparing grain alcohol, which comprises:
    a. cooking a dispersion of cereal grains in water under a pressure of between about 50 to 120 psig and at a temperature within the range of from about 300° to about 350° F. to obtain a mash of high cereal grain content, said grain consisting essentially of 97 to 99 percent corn;
    b. converting the mash obtained in (a) with a glucoamylase ferment produced by the propagation of the microorganism *A. awamori* NRRL 3112 on a mash obtained by cooking a dispersion of cereal grains, said ferment containing about 0.5 percent (w/v) of a compound selected from the group consisting of glutamic acid and monosodium glutamate;
    c. inoculating the converted mash with fermentation yeast; and
    d. fermenting the inoculated and converted mash for a sufficient period to produce grain alcohol.

4. A process according to claim 3 wherein the mash of high cereal grain content of step (a) contains about 24 grams of cereal grain for each 100 milliliters of mash.

5. A process according to claim 3 wherein the mash of step (a) contains corn and malt in proportions of from 97 to 99 percent by weight corn and 1 to 3 percent by weight of malt.

6. A process according to claim 3 wherein the cooking carried out in step (a) is for 3.2 minutes at a temperature of 320° F. and under a pressure of 80 psig.

7. A process for preparing grain alcohol, which comprises;
    a. cooking a dispersion of cereal grains in water under a pressure of between about 50 to 120 psig and at a temperature within the range of from about 300° to about 350° F. to obtain a mash of high cereal grain content, said grain consisting essentially of 97 to 99 percent corn;
    b. converting the mash obtained in step (a) above with a glucoamylase ferment produced by the propagation of the microorganism *A. awamori* NRRL 3112 on a mash obtained by cooking a grain dispersion consisting essentially of 97 to 99 percent corn, under a pressure of from 50 to 120 psig and at a temperature of from about 300° to about 350° F;
    c. inoculating the converted mash with fermentation yeast; and
    d. fermenting the inoculated and converted mash for a sufficient period to produce grain alcohol.

8. A process according to claim 3 wherein cooking in steps (a) and (b) is carried out for 3.2 minutes at a temperature of 320° F. and under a pressure of 80 psig.

9. A process according to claim 7 wherein said converted mash has added thereto from about 1 percent to about 3 percent by weight of malt.

10. A process according to claim 7 wherein said inoculating is carried out by admixing fermentation yeast with the glucoamylase ferment prior to addition of said ferment into the mash to be converted and fermented.

11. A process for producing glucoamylase ferment, which comprises;
    a. cooking a dispersion of cereal grains in water under a pressure of from about 50 to 120 psig and at a temperature of from 300° to 350° F. to obtain a mash of high cereal grain content consisting essentially of from 97 to 99 percent corn;

b. inoculating the mash obtained with the microorganism *A. awamori* NRRL 3112; and c. fermenting the inoculated mash for a period of time sufficiently long to produce a glucoamylase rich ferment.

12. A process according to claim 11, wherein cooking is carried out under a pressure of about 80 psig.

13. A process according to claim 11, wherein cooking of the dispersion is for 3.2 minutes at a temperature of 320° F. and under a pressure of about 80 psig.

14. A process according to claim 11, wherein said mash comprises about 24 grams of cereal grain for each 100 milliliters of mash.

15. A process according to claim 11, wherein said mash comprises corn and malt in proportions of from 97 to 99 percent by weight of corn and from 1 to 3 percent by weight of malt.

16. A process for producing glucoamylase ferment, which comprises;

a. cooking a dispersion of cereal grains in water under a pressure of from about 50 to 120 psig and at a temperature of from 300° to 350° F. to obtain a mash of high cereal grain content consisting essentially of from 97 to 99 percent corn;

b. adding a compound selected from the group consisting of glutamic acid and monosodium glutamate to the mash obtained in step (a);

c. inoculating the mash obtained in (b) above with the microorganism *A. awamori* NRRL 3112; and d. fermenting the inoculated mash for a period of time sufficiently long to produce a glucoamylase rich ferment.

17. A process according to claim 16, wherein the mash has added thereto 0.5 percent by weight of glutamic acid.

* * * * *